United States Patent [19]

Smuda et al.

[11] Patent Number: 4,929,765
[45] Date of Patent: May 29, 1990

[54] PREPARATION OF PHENYLACETALDEHYDES

[75] Inventors: Hubert Smuda, Heidelberg; Wolfgang Hoelderich, Frankenthal; Norbert Goetz, Worms, all of Fed. Rep. of Germany; Hans-Gert Recker, Irvine, Calif.

[73] Assignee: BASF Aktiengesellschaft, Ludwigshafen, Fed. Rep. of Germany

[21] Appl. No.: 274,930

[22] Filed: Nov. 22, 1988

[30] Foreign Application Priority Data

Nov. 27, 1987 [DE] Fed. Rep. of Germany ....... 3740270

[51] Int. Cl.$^5$ ...................... C07C 45/67; C07C 45/70
[52] U.S. Cl. ...................... 568/427; 568/41; 568/43; 568/63; 568/67; 568/627; 568/663; 568/637
[58] Field of Search ............... 568/427, 637, 427, 627, 568/637, 645, 41, 67, 63, 663

[56] References Cited

U.S. PATENT DOCUMENTS 3,860,614 1/1975 Watson ............................ 568/427
4,495,371 1/1985 Neri et al. ........................ 568/427

FOREIGN PATENT DOCUMENTS 1112040 5/1986 Japan ................................ 568/427

Primary Examiner—Warren B. Lone
Attorney, Agent, or Firm—Keil & Weinkauf

[57] ABSTRACT

Phenylacetaldehydes of the general formula I

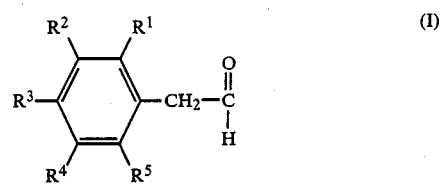

where $R^1$ to $R^5$ are each independently of the others hydrogen, alkyl, alkoxy, halogen, haloalkyl, haloalkoxy or haloalkylthio, by catalytic rearrangement in the presence of a zeolite, are prepared by reacting an epoxy of the formula II or a phenylglycol of the formula III

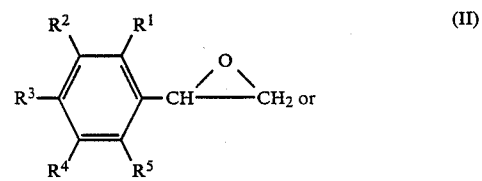

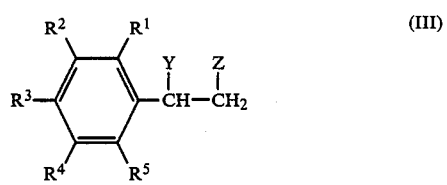

where Y and Z can be identical to or different from each other and are each hydroxyl, alkoxy, aryloxy or acyloxy, in the gas phase over a borosilicate zeolite catalyst at from 70° to 200° C. under reduced pressure.

6 Claims, No Drawings

PREPARATION OF PHENYLACETALDEHYDES

The present invention relates to a process for preparing phenylacetaldehydes from styrene oxides or phenylglycols in the presence of zeolites a catalysts.

It is known to prepare phenylacetaldehydes by dehydrogenation of phenylethanols with partial conversion and high-loss separation of starting materials and end product. Owing to the thermolability of phenylacetaldehydes, the fractionating step of the process leads to the formation of self-condensation products and thus to yield losses. Nor is it possible to prepare halogen-containing phenylacetaldehydes in this way, since halogen is eliminated under the reaction conditions.

Furthermore, the preparation of phenylacetaldehydes by catalytic rearrangement of styrene oxides is known. In general, again the reaction does not go to completion and difficult-to-remove by-products are obtained.

EP-A No. 100,117 describes the reaction of styrene oxide and of styrene oxides with alkyl or alkoxy substitution on the aromatic nucleus over titanium-containing zeolites in the liquid phase at 30° to 100° C. to give β-phenylacetaldehydes. The catalyst has to be expensively prepared from costly high-purity starting materials such as tetraalkyl orthosilicate, tetraalkyl orthotitanate and tetrapropylammonium hydroxide. There are also other prior art methods for rearranging epoxies to carbonyl compounds. For instance, cyclododecanone is obtained over Pd- or Rd-doped Al$_2$O$_2$ from epoxycyclododecane (Neftekhimiya 16 (1976), 250-254). It is expressly pointed out that zeolites are not suitable for this reaction. Similarly, the use of A-zeolites for the rearrangement of butylene oxide to butyraldehyde has been described (Hokkaido Daigaku Kogakubu Hokuku 67 (1973) 171-178). The selectivity (55-72%) leaves something to be desired. A-zeolite catalysts are difficult to regenerate following deactivation by coking, since at the temperatures of about 500° C. required for regeneration the crystal structure of these zeolites is destroyed.

It is an object of the present invention to develop a process for preparing the phenylacetaldehydes of the formula I from readily accessible starting materials with high conversions in the presence of a catalyst which shall be readily available and show high activity and high selectivity coupled with long times on stream. Moreover, the catalyst shall be readily regenerable in this process.

We have found that this object is achieved with a process for preparing a phenylacetaldehyde of the general formula I

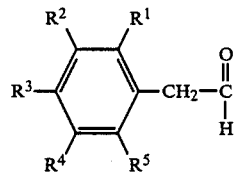
(I)

where R$^1$ to R$^5$ are each independently of the others hydrogen, alkyl, alkoxy, halogen, haloalkyl, haloalkoxy or haloalkylthio, by catalytic rearrangement in the presence of a zeolite, which comprises reacting an epoxy of the formula II or a phenylglycol of the formula III

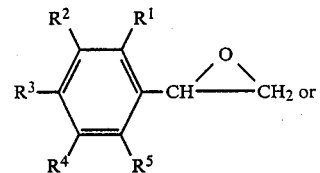
(II)

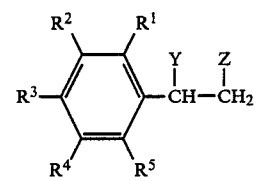
(III)

where Y and Z can be identical to or different from each other and are each hydroxyl, alkoxy, aryloxy or acyloxy, in the gas phase over a borosilicate zeolite catalyst at from 70° to 200° C. under reduced pressure.

The residence times over the catalyst in the course of the reaction should be less than 4 seconds (for example from 0.001 to 3.99 seconds), preferably less than one second (for example from 0.001 to 0.99 second). Preference is given to the use of borosilicate zeolites without Al-containing binder.

EP-A No. 228,675 already discloses a process of this type where zeolites of the pentasil, mordenite, erionite, chabazite or L-type are used and the reaction is carried out at from 200° to 500° C., preferably at from 200° to 400° C., under atmospheric pressure. Compared therewith the procedure according to the invention has the advantage in selectivity and catalyst lifetime, in particular if halogenated styrene oxides or phenylglycols are used.

General advantages of the process are that with complete conversion and selectivities >90% no separating problems result and very good yields are obtained even on conversion of halogen-containing starting materials. After the end products have been isolated, they can in general be used without additional purification. An additional advantage is the easy regenerability of the catalysts in the event of coking.

The reaction according to the invention proceeds in accordance with the following formula scheme:

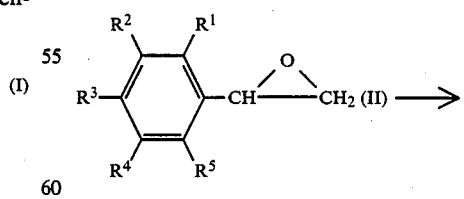

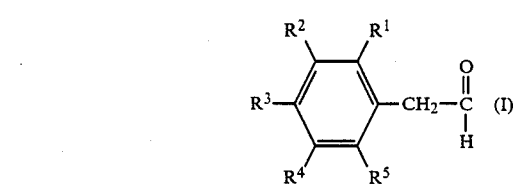

-continued

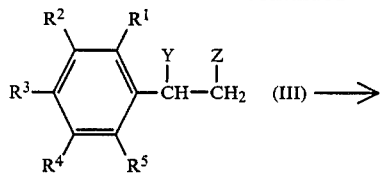

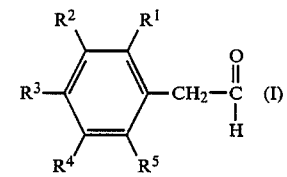

The substituents $R^1$ to $R^5$ in the formulae I to III are each independently of the others hydrogen, alkyl, alkoxy, halogen, haloalkyl, haloalkoxy and haloalkylthio.

The substituents Y and Z in the formula III can be identical to or different from each other and each be hydroxyl, alkoxy, aryloxy or acyloxy.

Epoxies used for the process according to the invention are for example styrene oxide, p-fluorostyrene oxide, p-chlorostyrene oxide, 2,4-difluorostyrene oxide, 3,4-difluorostyrene oxide, 2,4,5-trifluorostyrene oxide, o-, m- or p-trifluoromethylstyrene oxide, o-, m- or p-methylstyrene oxide, o-, m- or p-methoxystyrene oxide, 2,3,4,5-tetrafluorostyrene oxide, p-trifluoromethoxystyrene oxide, p-trifluoromethylthiostyrene oxide, 2-fluoro-6-chlorostyrene oxide, 2-fluoro-4-trifluoromethylstyrene oxide, 2-fluoro-4-trifluoromethoxystyrene oxide and 2-methyl-4-fluorostyrene oxide.

The phenylglycols used for the process according to the invention are for example phenylglycol, phenylglycol monomethyl ether, phenylglycol acetate and phenylglycol monophenyl ether.

The catalysts used are borosilicate zeolites. These can be synthesized for example at from 90° to 200° C. under autogenous pressure by reacting a boron compound, for example $H_3BO_3$ with a silicon compound, preferably finely divided silica, in an aqueous amine solution, in particular in a 1,6-hexanediamine or 1,3-propanediamine or triethylenetetramine solution, in the presence or absence of alkali metal or alkaline earth metal. It is also possible to use the isotactic zeolites described in DE-A No. 3,006,471. Instead of in aqueous amine solution the reaction can also take place in an ether solution, for example in diethylene glycol dimethyl ether, or in an alcohol solution, for example in 1,6-hexanediol.

The borosilicate zeolite obtained after isolation, drying at from 100° to 160° C., in particular at 110° C., and calcination at from 450° to 550° C., in particular at 500° C. to 540° C., can be molded with a binder in a ratio of 90:10 to 40:60% by weight, to extrudates or tablets. A suitable binder is silicon dioxide, preferably finely divided $SiO_2$. After molding, the extrudates or tablets are dried at 110° C./16 h and calcined at 500° C./16 h.

Suitable catalysts are also obtained when the isolated borosilicate zeolite is molded directly after drying and not subjected to a calcination until after molding. The borosilicate zeolites can be used in the pure form, without binder, as extrudates or tablets, the extrusion or peptization aids used being for example ethylcellulose, nitric acid, ammonia, amines, silicoesters and graphite or mixtures thereof.

If the borosilicate zeolite, on account of its manner of preparation, is present not in the catalytically active, acidic H form but in the Na form, the latter can be completely or partially converted into the desired H-form by ion exchange with ammonium ions and subsequent calcination, or by treatment with acids.

When the zeolitic catalyst becomes deactivated in the course of the reaction due to coking, it is advisable to regenerate the catalyst by burning off the coke deposit with air or with an air/$N_2$ mixture at from 400° to 500° C., in particular at from 500° C. to 540° C. This restores the catalyst to its initial activity level. By partial precoking it is possible to adjust the activity of the catalyst to optimum selectivity in respect of the desired reaction product.

To obtain as high a selectivity as possible, high conversion and a long time on stream, it is occasionally advantageous to modify the borosilicate zeolite. A suitable method of modifying comprises for example doping the unmolded or molded zeolites with metal salts by ion exchange or by impregnation.

Advantageously, doping is carried out by introducing the molded borosilicate zeolite into a riser pipe and passing an aqueous or ammoniacal solution of a halide or nitrite of the metal over it at from 20° to 100° C. Such an ion exchange can take place, for example, with the hydrogen, ammonium or alkali metal form of the zeolite. Another way of applying metal to the zeolite comprises impregnating the zeolitic material with an aqueous, alcoholic or ammoniacal solution of the metal or metal salt. Both ion exchange and impregnation are followed by at least one drying step, optionally by a further calcination.

An embodiment comprises for example dissolving $Cs_2CO_3$ in water and impregnating the molded or unmolded zeolite with this solution for a certain period, for example 30 minutes, and stripping the supernatant solution of water in a rotary evaporator. Thereafter the impregnated zeolite is dried at about 150° C. and calcined at about 550° C. This impregnating step can be carried out repeatedly until the desired metal content is obtained.

It is also possible to prepare an ammoniacal $Pd(NO_3)_2$ solution and to suspend the pure pulverulent zeolite therein at from 40° to 100° C. by stirring for about 2 h. After filtration, drying at about 150° C. and calcination at about 500° C., the zeolitic material thus obtained can be further processed with or without binders into extrudates, pellets or fluidizable material.

An ion exchange on the zeolite present in the H-form can also be carried out by introducing the zeolite in extruded or pellet form into a column and passing an ammoniacal $Pd(NO_3)_2$ solution over it in a recycle loop at slightly elevated temperatures of from 30° to 80° C. for from 15 to 20 hours. This is followed by washing with water, drying at about 150° C. and calcination at about 550° C.

For some metal-doped zeolites an aftertreatment with hydrogen is advantageous.

A further method of modifying the zeolite comprises treating the zeolite, which may be in molded or unmolded form, with an acid such as hydrochloric acid, hydrofluoric acid or phosphoric acid and/or steam.

The catalysts described here can optionally be used as from 2 to 4 mm extrudates or as tablets from 3 to 5 mm in diameter or as powders from 0.1 to 0.5 mm in particle size or in fluidizable form.

The conversion of the epoxies or glycols is carried out in the gas phase at from 70° to 200° C., in particular at from 120° to 170° C., using a weight hourly space velocity (WHSV) of from 0.1 to 30 h$^{-1}$, in particular of from 0.5 to 15 h$^{-1}$ (g of epoxy per g of catalyst per hour). In general, conversion and selectivity remain constant at increasing temperature, but decrease with increasing residence time over the catalyst. The reaction can be carried out in a fixed bed or fluidized bed.

The reaction is carried out under a reduced pressure of less than 1000 mbar, ie. at from 0.1 to 999 mbar.

The pressure range can be chosen in accordance with the boiling point of the substances to be converted. If for example substances having boiling points above 200° C. under atmospheric pressure are used, reduced pressure makes it possible to lower the boiling point along the vapor pressure curve to within the temperature range of from 70° to 200° C. For this reason the reduced pressure procedure widens the scope of application of the reaction in the gas phase.

However, in the case of starting materials whose boiling point under atmospheric pressure is below 200° C., the process under reduced pressure is advantageous because this reduces the residence time over the catalyst to less than one second. This can have a favorable effect on the selectivity.

Involatile or solid starting materials are used in dissolved form, for example in THF, toluene or petroleum ether solution. Dilution with the solvents mentioned is also possible.

After the reaction the phenylacetaldehydes are isolated from the reaction mixture in a conventional manner, for example by distillation; unconverted starting materials may be recycled into the reaction. Direct use of the reaction products is also possible owing to the very high yields. The process preferentially produces the compounds in monomer form. If oligomeric, for example trimeric, phenylacetaldehydes should also be formed they can be separated off and split into the desired monomers in a conventional manner.

The compounds accessible by the process according to the invention are important intermediates for bioactive compounds, for example insecticides such as resmethrin. They can also be processed by conventional methods, for example by oxidation with oxygen or by reduction, for example by catalytic hydrogenation or hydrogenating amination, into amines, alcohols and acids which in turn are useful intermediates.

The epoxies can be prepared either by epoxidation of the corresponding styrenes or from haloacetophenones by hydrogenation to chlorohydrins or bromohydrins and by subsequent cyclization in an alkaline medium. By reacting the epoxies with water, alcohols, carboxylic acids or phenols, it is possible to prepare further intermediates suitable for forming phenylacetaldehydes by rearrangement.

EXAMPLES p-Fluorostyrene oxide is isomerized over catalyst A to give p-fluorophenylacetaldehyde. The reactions are carried out under isothermal conditions in a tubular reactor (1.9 cm in internal diameter, 50 cm in length) in the gas phase. The weight hourly space velocity is 2.5 g of epoxy per g of catalyst per hour. The length of run is in each case 4 hours. The flow velocity in the tubular reactor is either adjusted by means of an N$_2$ stream in such a way that the residence time is 2 seconds, 1.5 seconds, or 1 second or adjusted in such a way by applying a water jet vacuum that the residence time is <0.3 seconds (see Tables 1 and 2).

TABLE 1

Selectivity of zeolite-catalyzed rearrangement of p-fluorostyrene oxide to p-fluorophenylacetaldehyde

| Residence T time | 180° C. | 160° C. | 140° C. |
|---|---|---|---|
| 2 seconds | 82% | — | — |
| 1.5 seconds | 90% | 90% | 92% |
| 1.0 second | 92% | — | — |

TABLE 2

Selectivity of zeolite-catalyzed rearrangement of p-fluorostyrene oxide to p-fluorophenylacetaldehyde: dependence of selectivity on weight hourly space velocity using catalyst A

| Residence time | 180° C., WHSV = 5 h$^{-1}$ | 180°, WHSV = 10 h$^{-1}$ |
|---|---|---|
| <0.3 second Catalyst A | 96.4% | 96.6% |

A borosilicate zeolite of the pentasil type is prepared by hydrothermal synthesis from 640 g of finely divided SiO$_2$, 122 g of H$_3$BO$_3$ and 8 kg of an aqueous 1,6-hexanediamine solution (mixture 50:50% by weight) at 170° C. under autogenous pressure in a stirred autoclave. After filtering and washing, the crystalline reaction product is dried at 100° C./24 h and calcined at 500° C./24 h. This borosilicate zeolite is composed of 94.2% by weight of SiO$_2$, and 2.3% by weight of B$_2$O$_3$.

This material is molded with a molding aid into 2 mm extrudates which are dried at 110° C./16 h and calcined at 500° C./24 h.

We claim:

1. A process for preparing a phenylacetaldehyde of the general formula I

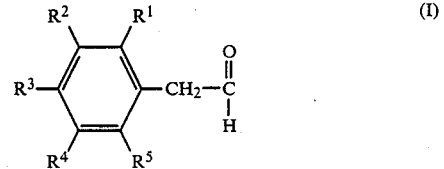

where R$^1$ to R$^5$ are each independently of the others hydrogen, , alkoxy, halogen, haloalkyl, haloalkoxy or haloalkylthio, by catalytic rearrangement in the presence of a zeolite, which comprises reacting an epoxy of the formula II or a phenylglycol of the formula III

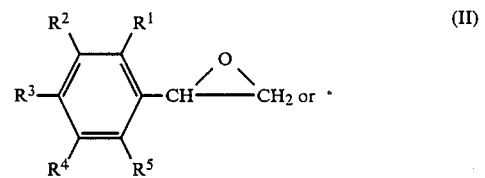

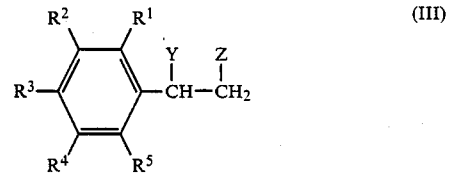

where Y and Z can be identical to or different from each other and are each hydroxyl, alkoxy, aryloxy or acyloxy, in the gas phase over a borosilicate zeolite catalyst at from 70° to 200° C. under reduced pressure at a residence time over the catalyst of less than 4 seconds.

2. A process as claimed in claim 1, wherein the reaction is carried out at from 0.1 to 999 mbar.

3. A process as claimed in claim 1, wherein the residence time over the catalyst in the course of the reaction is less than one second.

4. A process as claimed in claim 1, wherein a borosilicate zeolite without Al-containing binder is used.

5. A process for preparing a phenylacetaldehyde of the formula

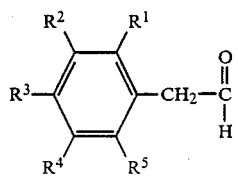 (I)

where $R^1$ to $R^5$ are each independently hydrogen, alkyl, alkoxy, halogen, haloalkyl, haloalkoxy or haloalkylthio wherein each of the alkyl groups is of low molecular weight, by catalytic rearrangement in the presence of a zeolite, which process comprises reacting an epoxy of the formula

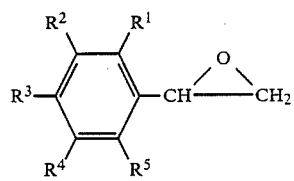 (II)

or a phenylglycol of the formula

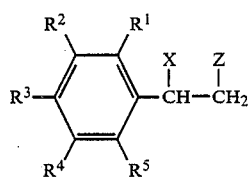 (III)

wherein each of $R^1$ to $R^5$ has the meaning set forth above and each of Y and Z can independently be hydroxyl, alkoxy, aryloxy or acyloxy wherein the carbonaceous radicals are of low molecular weight, in the gas phase over a borosilicate zeolite catalyst at from 70° to 200° C. under reduced pressure at a residence time over the catalyst of less than four seconds.

6. A process according to claim 5 wherein $R^1$ to $R^5$ are each independently hydrogen, methyl, methoxy, halogen, halomethyl, halomethoxy or halomethylthio, and each of Y and Z are independently selected from the group consisting of hydroxyl, methoxy, phenyloxy, and acyloxy.

* * * * *

UNITED STATES PATENT AND TRADEMARK OFFICE
CERTIFICATE OF CORRECTION

PATENT NO. : 4,929,765
DATED     : May 29, 1990
INVENTOR(S) : Hubert SMUDA et al.

It is certified that error appears in the above-identified patent and that said Letters Patent is hereby corrected as shown below:

Claim 1, second line following the structural formula I
(column 6, line 46)
"hydrogen, ," should read --hydrogen, alkyl,--

Signed and Sealed this

Thirtieth Day of July, 1991

Attest:

HARRY F. MANBECK, JR.

Attesting Officer

Commissioner of Patents and Trademarks